United States Patent
Reefman et al.

(10) Patent No.: US 6,370,490 B1
(45) Date of Patent: Apr. 9, 2002

(54) METHOD OF DETERMINING AN INTRINSIC SPECTRUM FROM A MEASURED SPECTRUM

(75) Inventors: Derk Reefman; William Jacques Jean Rey; Augustus Josephus Elizabeth Maria Janssen, all of Eindhoven (NL)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/592,059

(22) Filed: Jun. 12, 2000

(30) Foreign Application Priority Data

Jun. 14, 1999 (EP) .............................................. 99201878

(51) Int. Cl.[7] .............................................. G06F 17/16
(52) U.S. Cl. ........................................ 702/196; 356/327
(58) Field of Search ......................... 702/196; 356/327, 356/367

(56) References Cited

U.S. PATENT DOCUMENTS 5,612,783 A  * 3/1997 Hirsh .......................... 356/327

OTHER PUBLICATIONS

"Bayesian Interpolation" by David J.C. MacKay, Neural Computation 4, pp 415–447.

* cited by examiner

Primary Examiner—Kamini Shah

(57) ABSTRACT

In determining an intrinsic spectrum from a measured spectrum using the Maximum Entropy Algorithm, it is hardly or even not at all practical to determine the eigenvalues of an N×N matrix of large dimensions (N of the order of from $10^4$ to $10^5$). According to the invention such a large matrix is subdivided into a large number of much smaller partial matrices that are located on the diagonal or trace of the large matrix. The set of eigenvalues to be determined then consists of all eigenvalues of the partial matrices which can be determined much faster. Because of the Toeplitz-like character of the partial matrices, their eigenvalues can be determined very fast by Fourier transformation of a single row of such a matrix. Using the set of eigenvalues thus obtained, the intrinsic spectrum is determined by means of a minimizing algorithm. The convergence rate of the minimizing algorithm can be highly enhanced by adding a random noise value to the variables of the minimizing process and by decreasing that noise value to zero in a number of iteration steps.

4 Claims, 4 Drawing Sheets

METHOD OF DETERMINING AN INTRINSIC SPECTRUM FROM A MEASURED SPECTRUM

FIELD OF THE INVENTION

The invention relates to a method of determining an intrinsic spectrum f of radiation emitted by an object to be examined, which intrinsic spectrum f is represented by a set of N data points $f_1 \ldots f_N$ and is determined from a measured spectrum h which is represented by a set of M measuring points $h_1 \ldots h_M$ and is measured by means of an analysis apparatus having a given apparatus transfer function G in the form of an M×N matrix, which method includes the following steps:

a) forming an approximated intrinsic spectrum g of N data points $g_1 \ldots g_N$;

b) determining a measure of misfit $\chi^2$ between the approximated intrinsic spectrum, convoluted with the apparatus transfer function G, and the measured spectrum;

c) determining the value of a predetermined regularizing function S by inserting the approximated intrinsic spectrum in this function;

d) forming a functional $F=\chi^2+\alpha S$ containing a regularizing constant $\alpha$;

e) solving the regularizing constant $\alpha$ from said functional, the N eigenvalues $\lambda_1 \ldots \lambda_N$ of an N×N auxiliary matrix A formed from the apparatus transfer function and the approximated intrinsic spectrum being determined during said solution process;

f) executing a minimizing process on the functional F with the last regularizing constant $\alpha$ found, using the N data points of the intrinsic spectrum as variables, the N data points thus found constituting a next approximated intrinsic spectrum;

g) repeating the steps b) to f), if necessary, until a predetermined convergence criterion has been satisfied;

h) identifying the approximated intrinsic spectrum then valid as the intrinsic spectrum searched.

The invention also relates to a storage medium which can be read by a computer and is provided with a computer program for carrying out said method, and also to a radiation analysis apparatus which is suitable to carry out the method.

DESCRIPTION OF PRIOR ART

An algorithm for carrying out such a method is known from the article "Bayesian Interpolation" by David J. C. MacKay, Neural Computation 4, pp. 415–447. Algorithms of this kind are known as "Maximum Entropy Algorithms".

The cited article, notably chapter 4 thereof, describes how the intrinsic variation of a quantity can be determined from a set of measuring values of the relevant quantity which suffer from noise and other disturbing effects, i.e. the variation of this quantity if all disturbing effects exerted by, for example, the measuring equipment and/or static processes were removed.

A situation of this kind occurs, for example, during the measurement of an intensity spectrum as is done in X-ray diffraction. An object to be examined (a crystalline sample) is then irradiated by X-rays which are emitted again by the sample in a manner which is characteristic of the relevant material. The intensity of such emitted radiation is dependent on the angle at which the radiation is incident on the lattice faces of the crystalline material to be examined. An intensity spectrum of the emitted radiation is measured as a function of the take-off angle by moving an X-ray detector around the sample during the measurement.

In order to achieve a suitable angular resolution of the measurement, a limiting gap with a gap width of the order of magnitude of from 20 to 200 $\mu$m is arranged in front of the detector; in the case of a circumscribed circle having a radius of 30 cm this means that a measurement of a spectrum of one revolution yields a number of measuring points N of the order of magnitude of from $N=10^4$ to $N=10^5$.

As is known from the practice of measurement by means of such apparatus, the spectrum of measuring points is the convolution of the intrinsic spectrum with the apparatus transfer function, possibly increased by noise and contributions by other disturbing effects. The transfer function takes into account the effect of all optical elements in the radiation path from the radiation source to the detector, notably the finite width of the detector slit; furthermore, it is in general also dependent on the location of the measurement (i.e. the magnitude of the take-off angle) so that, as is known for such apparatus, for numerical processing the transfer function takes the form of an M×N matrix (where N and M are of the same order of magnitude), i.e. a matrix with from $M \times N=10^8$ to $M \times N=10^{10}$ matrix elements.

The determination of the intrinsic spectrum according to the algorithm disclosed in the cited article by MacKay is based on an approximation of the intrinsic spectrum. This approximation may be based on prior theoretical knowledge of the spectrum to be measured, but the measured spectrum consisting of a set of M measuring points may also be taken as the approximated intrinsic spectrum; in order to obtain a set of N points, interpolation can be performed between the M measuring points (if M<N) or a part of the M measuring points can be ignored (if M>N). Subsequently, a measure of misfit $\chi^2$ is formed between the approximated intrinsic spectrum, convoluted with the apparatus transfer function, and the measured spectrum. Because of the absence of, for example noise and other statistical functions, this measure of misfit does not have the value zero.

In conformity with the Maximum Entropy Algorithm rule there is formed a functional $F=\chi^2+\alpha S$ in which the regularizing function S is dependent on the N data points of the intrinsic spectrum. The appearance of this regularizing function S is dependent on the nature of the process to be measured; in the case of X-ray diffraction, the appearance of this function may be $\Sigma(f_i)*\log(f_i)$, in which the quantities $f_i$ represent the intensities of the measuring points. The regularizing function S includes a factor $\alpha$ which is referred to as the regularizing constant. According to the Maximum Entropy Algorithm, the functional F must be minimized in dependence on the value of the data points of the intrinsic spectrum. The spectrum of data points at which the functional F is minimum then constitutes the intrinsic spectrum searched. For numerical execution of the minimizing process, however, it is first necessary to determine the value of the regularizing constant $\alpha$; moreover, an assumption must be made in respect of numerical initial values of the intrinsic spectrum, both in the regularizing function S and in the quantity $\chi^2$. As has already been stated, the measured spectrum can often be chosen for the numerical initial values of the intrinsic spectrum.

The cited article describes a process for solving the regularizing constant $\alpha$ from the functional F. Therein, an N×N auxiliary matrix is first determined from the apparatus transfer function and the approximated intrinsic spectrum. The process of forming the auxiliary matrix A is described in chapter 4.3 of the cited article. The set of eigenvalues of this auxiliary matrix is determined. A relation can then be derived between the regularizing constant $\alpha$ and the set of eigenvalues $\lambda_1 \ldots \lambda_N$, so that the regularizing constant $\alpha$ can be determined from this relation. This process is described notably in chapter 4.4 of the cited article; said relation is found by equating the formulas (4.8) and (4.9) described therein; it then follows that:

$$2\alpha S = \sum_{i=1}^{i=N} \frac{\lambda_i}{\lambda_i + \alpha} \quad (1)$$

(The quantity $E_W^{MP}$ stated in the cited article equals the regularizing function S). The value of the regularizing constant $\alpha$ can then be determined from expression (1) by means of standard solution methods. The value thus found can be inserted in the functional F, after which the minimum value of the functional F is determined in known manner, the N data points of the intrinsic spectrum then being the variables of the functional F. Those values of the data points at which the minim of F occurs constitute a better approximation of the intrinsic spectrum than the values of the initially selected approximated intrinsic spectrum. Depending on the desired precision of the final result, it can then be decided that the approximated intrinsic spectrum thus determined will be the intrinsic spectrum searched; in that case the calculations need not be continued. However, it may also be decided to continue the calculations; the approximated intrinsic spectrum determined thus far then forms the starting point of a next iteration cycle. Such iteration cycles can be repeated until the convergence criterion imposed by the desired precision is satisfied.

The cited article by MacKay does not provide information regarding the dimensions of the auxiliary matrix A. However, it is generally known that the calculation time required to determine the eigenvalues of a matrix increases as the third power of the linear dimension of such a matrix. In the case of matrices such as they may occur, for example in the acquisition of intensity spectra, the value of N or M, so the dimension of the matrix A, may be of the order of magnitude of from $10^4$ to $10^5$. (The quantities M and N are of the same order of magnitude.) The determination of the eigenvalues of a matrix having such dimensions is no longer possible in practical circumstances. Notably for analytic equipment as used for standard laboratory analysis, it is desirable to execute the associated calculations with a customary personal computer with a calculation time which is of the same order of magnitude as the time required for executing the associated measurement.

SUMMARY OF THE INVENTION

It is an object of the invention to provide a method of the kind set forth in which the determination of the eigenvalues of matrices of large dimensions is significantly faster than in the standard prior art methods.

To this end, the method according to the invention is characterized in that for the determination of the N eigenvalues $\lambda_1 \ldots \lambda_N$ of the N×N auxiliary matrix A, the auxiliary matrix is subdivided into a number of L partial auxiliary matrices $P_j$ (j=1 . . . L) which are situated around the diagonal of the auxiliary matrix A, and that the eigenvalues of each partial auxiliary matrix $P_j$ are determined separately, the set of eigenvalues $\lambda_1 \ldots \lambda_N$ of the N×N auxiliary matrix A consisting of the set of all eigenvalues of the partial auxiliary matrices $P_j$.

The invention is based on the recognition of the fact that the apparatus transfer function G has the form of a M×N matrix (where M is the number of measuring points) for many spectroscopic measurements, but that the numbers in this matrix are much greater in the direct vicinity of the diagonal than the numbers which are situated further away. This is due to the fact that the width of the detector slit of such a spectroscopic apparatus is generally very small relative to the total measuring trajectory, so that a point of the intrinsic spectrum which is situated far from the slit position has only a (very) slight effect on the intensity measured in the relevant slit position. Thus, only a narrow band of numbers around the diagonal is of importance in the rows of the matrix.

The formation of the N×N auxiliary matrix A from the apparatus transfer function and the approximated intrinsic spectrum is performed in such a manner that the appearance of this auxiliary matrix has a structure which is comparable to that of the apparatus transfer function G, so that A also has a band structure.

The invention is also based on the recognition of the fact that the determination of the eigenvalues of such an auxiliary matrix A can be performed by replacing said auxiliary matrix by a comparatively large number of much smaller partial auxiliary matrices P which succeed one another along the diagonal of the auxiliary matrix and whose diagonals lie on that of the auxiliary matrix. The dimensions of such partial auxiliary matrices are chosen to be such that the elements in each row of said partial auxiliary matrices contain the large values of the corresponding row of the auxiliary matrix and that, consequently, the elements of the relevant row which lie outside the partial auxiliary matrix have a value such that it can be ignored for all practical purposes. The determination of the set of eigenvalues of such a (much) smaller partial auxiliary matrix is much easier than that of the large auxiliary matrix. The gain in respect of calculation time can be illustrated on the basis of the following numerical example: when the auxiliary matrix A is subdivided into 100 partial auxiliary matrices P, the calculation time for determining the eigenvalues of one partial auxiliary matrix becomes $10^6$ times shorter, so $10^4$ times shorter for all 100 partial auxiliary matrices. A substantial gain is thus realized in respect of the calculation time required to determine the eigenvalues.

By performing an experimental check on the basis of a known spectrum (or by once applying a conventional, time-consuming diagonalizing algorithm to the auxiliary matrix), it can be checked whether the precision thus achieved in determining the eigenvalues of the auxiliary matrix A suffices for practical purposes. Such adequate precision can also be demonstrated theoretically.

In a version of the invention the eigenvalues of the partial auxiliary matrices are determined by determination of the Fourier transform of an arbitrary row of each of said partial auxiliary matrices.

The insight on which this aspect of the invention is based consists in that said narrow band of elements along the diagonal of the auxiliary matrix varies only slowly in value, i.e. even though the numbers in said band of numbers have been shifted one location between two successive rows, these numbers exhibit only small differences per row. This small difference per row is due to the fact that, because of the small width of the detector slit, the transfer from the emissive sample to the detector varies only gradually as a function of the angular position of the detector. A matrix exhibiting both these phenomena (i.e. a band structure and a small difference between the elements of neighboring rows along the diagonal) resembles a so-called Toeplitz matrix. As is known, a Toeplitz matrix is a matrix whose first row consists of arbitrary numbers. The subsequent row is obtained by shifting all elements of the previous row through one location in the row; the void then arising at one end is filled with an arbitrary element and the element at the other end is deleted. (When the void arising at one end is filled with the element deleted at the other end, a so-called "circulant continuation" is concerned). This phenomena is repeated for all subsequent rows of the matrix.

The auxiliary matrix is distinct from a Toeplitz matrix in that a given variation of the value of the elements occurs along the matrix diagonal in the auxiliary matrix. As has already been described, the determination of the eigenvalues of such an auxiliary matrix is performed by replacing said auxiliary matrix by a comparatively large number of much smaller partial auxiliary matrices which succeed one another along the diagonal of the auxiliary matrix and whose diagonals lie on that of the auxiliary matrix. The dimensions of said partial auxiliary matrices must be chosen to be such that the variation of the values of the elements along their diagonal is negligibly small for all practical purposes. Because such partial auxiliary matrices approximate the Toeplitz structure much better than the auxiliary matrix itself, a theorem which holds for Toeplitz matrices can be applied to such partial auxiliary matrices; according to theorem the eigenvalues of a Toeplitz matrix with a circulant continuation exactly equal the coefficients of the Fourier transform of an arbitrary row of the relevant matrix. Even though the partial auxiliary matrices need not be subjected to a circulant continuation in practice, the eigenvalues obtained by Fourier transformation constitute a suitable approximation of the exact eigenvalues of the partial auxiliary matrices. To those skilled in the art it will be generally known that the calculation time for determining the eigenvalues by means of Fourier transformation corresponds to $N*\log(N)$ (in which N is the dimension of the matrix) instead of $N^3$ as in the case of conventional determination of eigenvalues. The determination of the eigenvalues of the partial auxiliary matrices is thus reduced to the determination of the Fourier coefficients which is far less intensive in respect of calculation work, i.e. to the determination of the discrete Fourier transform of each time one matrix row of each of the partial matrices.

Ignoring the values in the auxiliary matrix which are not included in a partial auxiliary matrix, introduces a first error in the determination of the eigenvalues. Moreover, the determination of the eigenvalues of the partial auxiliary matrices by Fourier transformation (actually by equating the partial auxiliary matrices with the circulant continuation of a Toeplitz matrix) introduces a second error. A further advantage achieved by this version of the invention consists in that the first and the second error oppose one another, so that the resultant error is smaller than each of said errors individually.

According to a further version of the invention, the eigenvalues of the partial auxiliary matrices are determined by determining the Fourier transform of the mean of at least two arbitrary rows of each of said partial auxiliary matrices.

Because of this step, the actual eigenvalues are approximated even better since a given variation of the values of elements of the different rows is compensated because a mean row is thus used.

According to a further version of the invention, an amount which is arbitrarily distributed among the measuring points is added to the measuring points of the set of M measuring points during the execution of the minimizing process.

During the determination of the minimum of the functional F it may occur that, after a given iteration step in the minimizing process, the variation of this functional around the minimum is such that during a next iteration step either an extremely small further approximation of the minimum is realized (in the case of a very flat variation of the functional in said range, or that during a next iteration step the minimum is passed and the process is returned to the original iteration point again by the subsequent iteration step (in the case of a very acute variation of the functional in said range). In both cases the approximation of the minimum is very slow or even non-existent. Such undesirable phenomena can be avoided by the addition of artificial noise which decreases to zero as the minimizing process progresses.

BRIEF DESCRIPTION OF THE DRAWING

The invention will be described in detail hereinafter with reference to the Figures. Therein.

DETAILED DESCRIPTION OF THE PREFERRED EMBODIMENTS

The invention will be described on the basis of an X-ray diffraction device which forms a spectrogram to be processed in accordance with the invention. However, it is to be noted that the present invention is by no means restricted to X-ray diffractograms but can also be used for other spectra such as optical or X-ray fluorescence spectrograms.

Figure 1:
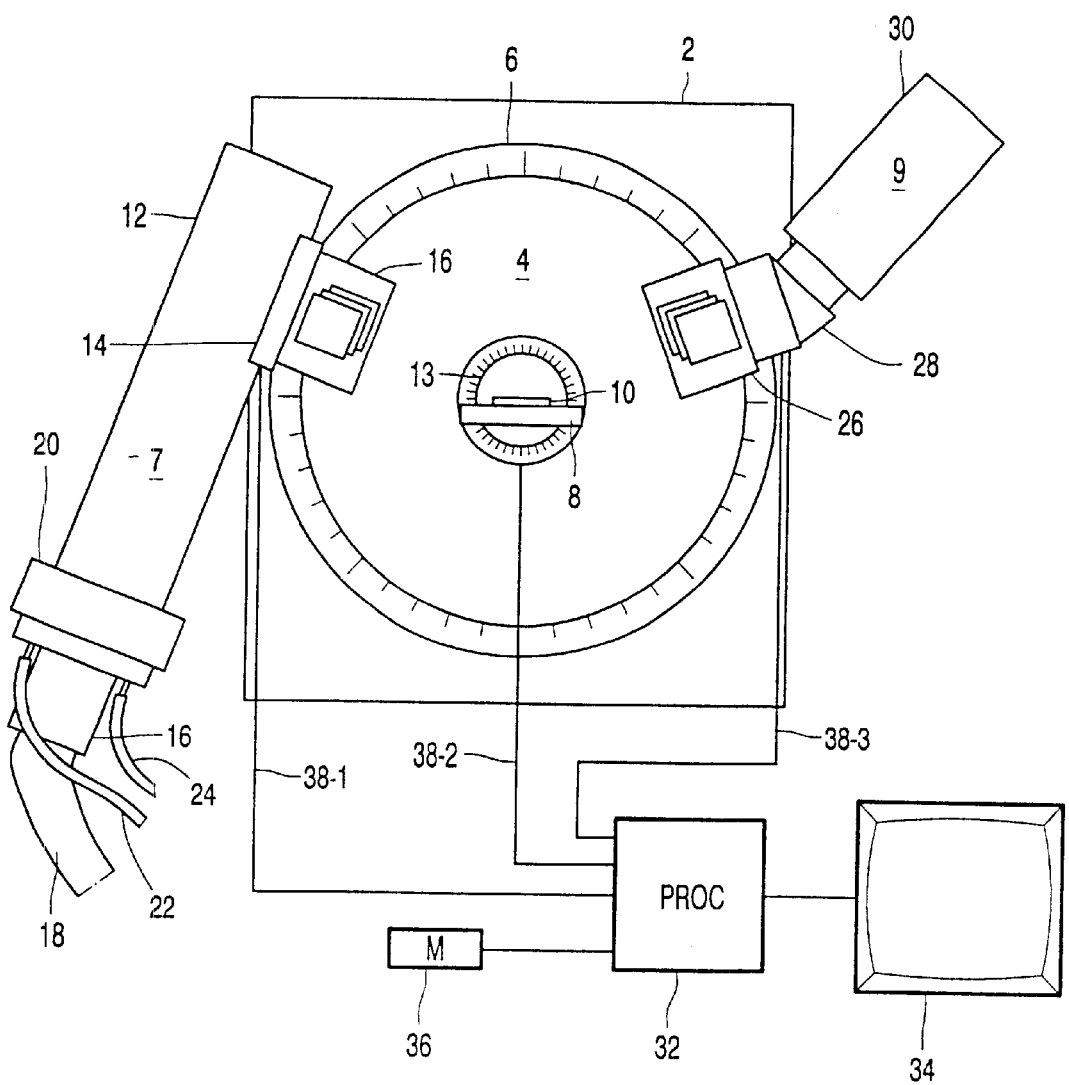
FIG. 1 is a diagrammatic representation of an X-ray diffraction device which is suitable for carrying out the method according to the invention.

FIG. 1 shows an X-ray diffraction device. A goniometer 4 is mounted on a frame 2. The goniometer 4 is provided with a graduation for measuring the angular rotation of the X-ray source 7 mounted thereon and of the detector device 9 which is also mounted thereon. The goniometer is also provided with a sample holder 8 on which a sample 10 is arranged. A graduation 13 is provided for cases where measurement of the angular rotation of the sample is important. The X-ray source 7 includes a holder 12 for an X-ray tube which is not shown in this Figure and is mounted in the holder by way of a mounting ring 20. The X-ray tube includes a high-voltage connector 16 for the supply of the high-voltage and the filament current for the X-ray tube via a high-voltage cable 18. The inlet and outlet ducts 22 and 24 for the cooling water of the X-ray tube are provided at the same side of the X-ray tube. The tube holder 12 also includes an exit window 14 for X-rays and a unit 16 for parallelizing the X-ray beam (a Soller slit). The detector device 9 consists of a holder 26 for a Soller slit, a holder 28 for a monochromator crystal, and a detector 30. If the X-ray source and the detector are both rotatable about the specimen (as indicated in the Figure), it is not necessary for the specimen to be arranged so as to be rotatable. However, it is alternatively possible to mount the X-ray source so as to be stationary, as may sometimes be necessary in the case of bulky and heavy X-ray sources. In that case the specimen holder and the detector should both be rotatable.

The X-ray diffraction device as shown in FIG. 1 also includes a processing device for processing the various measured data. The processing device consists of a central processing unit 32 whereto there are connected a memory unit 36 and a monitor 34 for the presentation of the various data and for the display of the measured and calculated result. Needless to say that the memory unit 36 need not be constructed so as to be separate and that it may form part of the central processing unit 32. The X-ray source 7 mounted on the goniometer 4, the detector device 9 and the specimen holder 8 are all provided with a unit (not shown) for determining the angular position of the relevant element relative to the graduation of the goniometer. A signal representing this angular position is applied to the central processing unit 32 via connection leads 38-1, 38-2 and 38-3. The memory unit 36 contains the data required for the execution of the method as will be described in detail hereinafter with reference to FIG. 2. Using the X-ray diffraction device shown in FIG. 1, a diffractogram is formed in known manner for a specimen whose diffraction spectrogram is to be determined, i.e. the intensity and the angular position of the various diffraction lines are determined by traversing the entire angular range $0 \leq \theta \leq 2\pi$.

The method according to the invention will be described in detail hereinafter on the basis of the flow chart shown in FIG. 2. In conformity with the maximum entropy algorithm, a first estimate is made of the intrinsic spectrum to be determined from the measured values. This first estimate is referred to as the first choice of the approximated intrinsic spectrum. The intrinsic spectrum f and the approximated intrinsic spectrum g are both represented by a vector with N characteristic numbers, because the spectrum consists of a number of N values. The measured spectrum h is represented by a vector with M characteristic numbers, because this spectrum consists of a number of M measuring points. The measured spectrum is thus represented by the vector $h=(h_1 \ldots h_M)$, in which $h_i$ is the intensity at the $i^{th}$ measuring point; analogously, the intrinsic spectrum is represented by the vector $f=(f_1 \ldots f_N)$ and the approximated intrinsic spectrum by the vector $g=(g_1 \ldots g_N)$.

The first choice of the approximated intrinsic spectrum g may be comparatively arbitrary. If nothing were known as regards the appearance of the intrinsic spectrum f, even a completely flat variation would be feasible for this first choice, so all values $f_1 \ldots f_N$ equal to one another. However, because it may be assumed that the measured spectrum h is a reasonably accurate rendition of the intrinsic spectrum, it will be natural to select the measured spectrum h as the first choice of the approximated intrinsic spectrum g. This choice is represented in block 2—2 in the flow chart of FIG. 2.

In order to apply the maximum entropy algorithm, a functional F must be formed as follows:

$$F = \chi^2 + \alpha S \quad (2)$$

In the expression (2) for F, $\chi^2$ is a measure of the misfit between the approximated intrinsic spectrum g convoluted with the apparatus transfer function G (in the form of an M×N matrix) and the measured spectrum h. (The apparatus transfer function G has the form of an M×N matrix). S is called the regularizing function; this function will be described in detail hereinafter and so will the quantity a which is a parameter in the minimizing process of the functional F according to the maximum entropy algorithm. As is customary for the determination of misfit, the following expression is used for $\chi^2$:

$$\chi^2 = \sum_{i=1}^{i=N} \left\{ \frac{(\overline{G} \cdot \overline{f})_i - h_i}{\sigma_i} \right\}^2 \quad (3)$$

In the expression (3) $\sigma_i$ is a measure of the standard deviation in the values of the characteristic numbers $h_i$ of the vector h, which standard deviation is determined by the physical properties of the measured quantity. In the case of X-ray spectra, the standard deviation is approximately equal to the root of the intensity, so approximately the root of the measuring value, i.e. the root of the number of counting pulses of the detector.

A given freedom exists as regards the choice of the form of the regularizing function S; this form is preferably chosen in dependence on the problem to be solved. When an intrinsic diffraction spectrum is to be determined from a measured diffraction spectrum, the following expression is used:

$$S = \sum_{i=1}^{i=N} f_i \log\left(\frac{f_i}{m_i}\right) \quad (4)$$

In the expression (4) the vector $m=(m_1 \ldots m_N)$ is a function expressing a priori knowledge, if any, of the intrinsic spectrum f to be determined. When the regularizing function S has the appearance of expression (4), the term entropic function S is also used. In the case of, for example an X-ray diffraction spectrum, the angular values diffraction for which maxima are to be expected could be known in advance. In that case the characteristic numbers $m_i$ of the vector m can be assigned a comparatively high value in these locations whereas a comparatively low value is assigned between said angular values.

Combination of the expressions (2), (3) and (4), ultimately yields the expression to be minimized for the functional F:

$$F(\overline{f}) = \sum_{i=1}^{i=N} \left\{ \frac{(\overline{G} \cdot \overline{f})_i - h_i}{\sigma_i} \right\}^2 + \alpha \sum_{i=1}^{i=N} f_i \log\left(\frac{-f_i}{m_i}\right) \quad (5)$$

The aim is for such a final choice of the approximated intrinsic spectrum that an as small as possible misfit occurs between the approximated intrinsic spectrum and the intrinsic spectrum to be determined; this would be the case for $\chi^2=0$. However, as is generally known in the technique of the maximum entropy algorithm, this is not the most probable value for $\chi^2$; therefore, the aim is for the value $\chi^2=1$. However, in this situation ($X^2=1$) one vector f is not yet unambiguously determined; this can be readily understood because the result $\chi^2=1$ can be obtained by means of many combinations of $f_1$ to $f_N$. In that case it is said that the minimizing problem is indeterminate. In order to eliminate the indeterminateness, the term $\alpha S$ is included in the functional, S being said function of f and m and the quantity $\alpha$ being a parameter for optimizing the minimizing process.

Prior to the minimizing process, however, first the regularizing constant $\alpha$ must be determined. To this end, in conformity with the Maximum Entropy Algorithm as described in said article by MacKay, first an N×N auxiliary matrix A is determined from the apparatus transfer matrix G and the approximated intrinsic spectrum g. The process of forming this auxiliary matrix is described in chapter (4.3) of the cited article which states that for the auxiliary matrix A it holds that: A=αC+βB, in which C=$\nabla\nabla E_W$ and B=$\nabla\nabla E_D$; the quantity $E_W$ therein represents the regularizing function S and the quantity $E_D$ represents the measure of misfit $\chi^2$ used in the present description; according to the present invention, however, β=1 may be taken, because the standard deviations $\sigma_i$ are known. Thus it holds that: A=α($\nabla\nabla$S)+$\nabla\nabla(\chi^2)$. A further elaboration of the latter representation yields the following expression for A as a function of G and f:

$$A_{ij} = 2\sum_{l=1}^{l=N} \frac{G_{li}G_{lj}}{\sigma_l^2} \sqrt{\frac{f_i f_j}{m_i m_j}} \qquad (6)$$

The calculation of $A_{ij}$ in conformity with the expression (6) for all values of i and j then yields the complete N×N auxiliary matrix A. This process is shown in the block 2-4 in the flow chart of FIG. 2.

In case the apparatus transfer matrix G is rather acute (i.e. the matrix elements in the direct vicinity of the diagonal have a comparatively high value and the other elements have a comparatively low value), as in the case of spectroscopic equipment, it will be evident to those skilled in the art that the auxiliary matrix A has a structure which is comparable to that of the apparatus transfer fimction G, i.e. that A also has a band structure where only small differences occur between two successive rows, except for the fact that the numbers in the numeric band have been shifted one position between two successive rows.

When the minimizing process for the functional F nears the end value, on the basis of the approximated intrinsic spectrum valid in that state a new estimate is formed for the regularizing constant α, after which the entire calculation process can be repeated, if desired, until a predetermined convergence criterion is met.

In order to enable determination of the eigenvalues of the auxiliary matrix A in accordance with the invention, the auxiliary matrix is subdivided into a comparatively large number L of smaller matrices $P_j$, where j=1 . . . L, said matrices being referred to as partial auxiliary matrices which are situated successively along the diagonal of the auxiliary matrix A, so that the diagonals of the matrices $P_j$ lie on that of the auxiliary matrix. This process is represented in the block 2-6 in the flow chart of FIG. 2. The dimensions of the partial auxiliary matrices $P_j$ are chosen to be such that the elements in each row of the partial auxiliary matrices contain the high values of the corresponding row of the auxiliary matrix A and that, consequently, the elements of the relevant row which lie outside the partial auxiliary matrix have a value such that it can be ignored for all practical purposes. The dimensions of the partial auxiliary matrices are thus co-determined by the properties of the auxiliary matrix A, so of the apparatus transfer matrix G, and by the precision desired for the intrinsic spectrum to be determined.

Because the partial auxiliary matrices $P_j$ have a Toeplitz-like appearance as described above, the eigenvalues of these matrices can be closely approximated by determining the Fourier transform of an arbitrary row, the eigenvalues then being substantially equal to the Fourier coefficients thus found. This process is represented in the block 2-8 in the flow chart of FIG. 2. If a higher accuracy is desired for this determination of the eigenvalues, the Fourier transformation can also be applied to a row formed by taking the mean of two or more rows of the relevant partial auxiliary matrix. The described process for determining the eigenvalues of a partial auxiliary matrix is carried out for all L partial auxiliary matrices, so for j=1 . . . L. The set of N eigenvalues thus obtained by forming the combination of L groups of eigenvalues then represents the searched set of N eigenvalues of the auxiliary matrix A, see block 2-10 in FIG. 2.

It can be demonstrated experimentally that the set of N eigenvalues obtained by means of the described process constitutes a suitable approximation of the set of exact eigenvalues. This is possible by exact diagonalization of a known matrix having a band structure. The fact that such exact diagonalization is a very time-consuming process, is not objectionable, because it need be performed only once or no more than a few times in order to demonstrate that the approximative method is sufficiently accurate. The eigenvalues obtained by way of the exact diagonalization can then be compared with the eigenvalues obtained by means of the described approximative method. It has been found that adequate accuracy is obtained for all practical purposes.

The value of the regularizing constant α is then determined by means of the expression (1), see block (2-12), after which the minimizing process for the functional F can be carried out. For the minimizing process, as carried out per iteration, a known algorithm can be used, for example the known "steepest descent" algorithm. Algorithms of this kind are generally known and need not be further explained herein.

As has already been described, it may happen that during the minimizing process the convergence is impeded by the shape of the convergence curve. In those cases the minimum is approximated very slowly or even not at all. In order to avoid such undesirable phenomena, artificial noise is added; this noise decreases to zero as the minimizing process progresses. This process of decreasing noise addition is based on the known process of "homotopic continuation". This process can be summarized as follows. The functional F to be minimized is dependent on the vector f, so F=F(f). If the convergence is too slow or even completely absent during the minimizing of this functional, a different functional F'=F'(f,a) is searched which is dependent not only on the vector f but also on a homotopic parameter a, so that this F' suitably converges for a given constant value of a (for example, 1). For F' such a function rule must be chosen that F'(f0)=F(f). The value of the homotopic parameter a can then be gradually decreased to zero during the iterations; the value of f for which F'(f,0) is minimum then also represents the value of f for which the functional F(f) to be minimized is minimum. This aspect of the invention is based on the recognition of the fact that a noise-like value can be taken as the homotopic parameter a, for example a quantity of noise with a Gaussian distribution. This quantity can be obtained by adding an arbitrary value to all values $h_1 \ldots h_N$. The arbitrary values are obtained, for example by choosing each time an arbitrary value $\epsilon_i$ from a set of values by means of a known random process; said set of values then has a Gaussian distribution with a variance a around the mean value zero. After the functional F' has been minimized by means of the values $h_i+E_i$ thus obtained, a new, smaller value is chosen for the homotopic parameter a. It is handy to reduce the original value of a by a given factor, for example 0.9, for this purpose and to repeat the described process; this process is then continued until ultimately convergence of the minimizing process is achieved for a value zero of the convergence parameter a. The described process is indicated in block 2-14 in the flow chart of FIG. 2. A value of the approximated intrinsic spectrum is thus found for which the functional F is minimum, see block 2-16 of FIG. 2. Using this value, subsequently it is determined whether a predetermined convergence criterion (block 2-18 of FIG. 2) has been satisfied.

Figure 2:
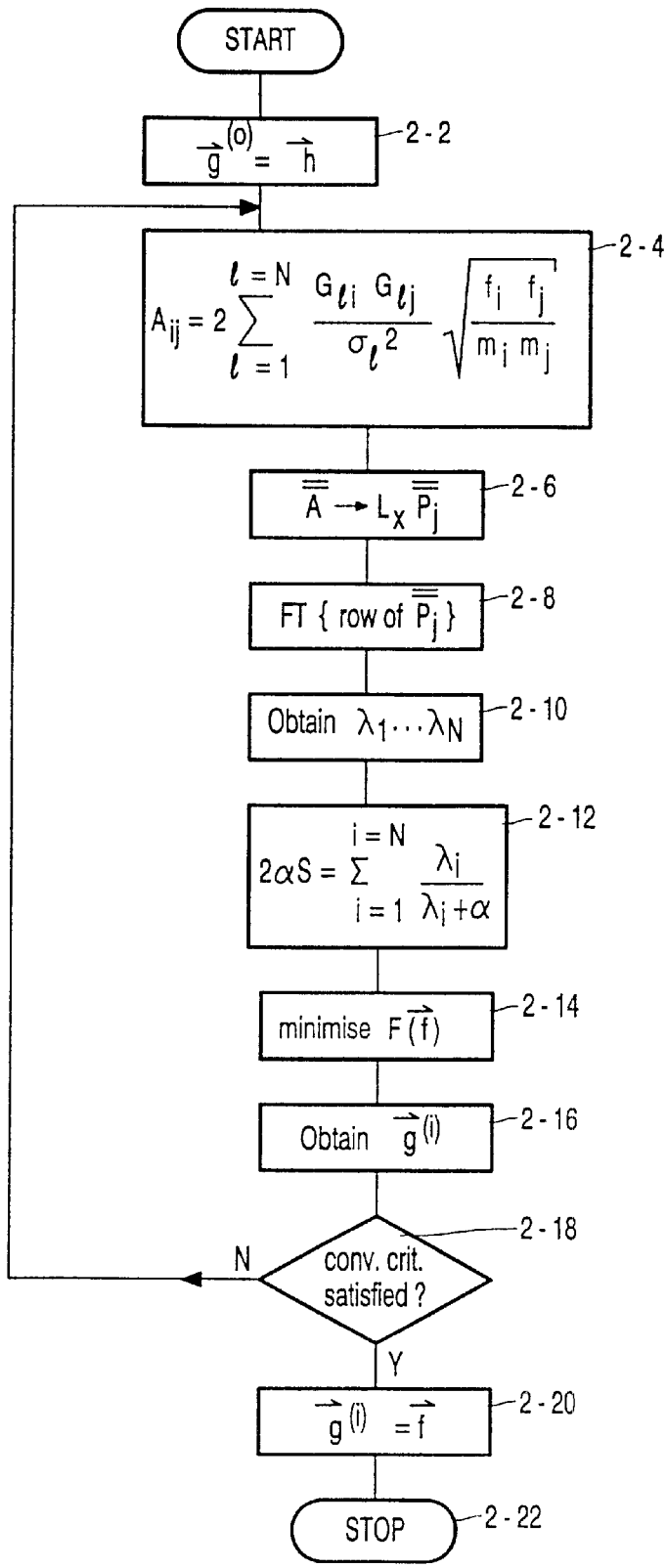
FIG. 2 shows a flow chart illustrating the various steps of the method according to the invention.

When the convergence criterion has been satisfied, the value of the approximated intrinsic spectrum then valid is identified as the intrinsic spectrum to be determined, see block 2-20 of FIG. 2. If the convergence criterion has not yet been satisfied, the entire procedure is repeated as from the block 2-4 until the convergence criterion has een satisfied. After that the process is terminated, see block 2-22.

Figure 3:
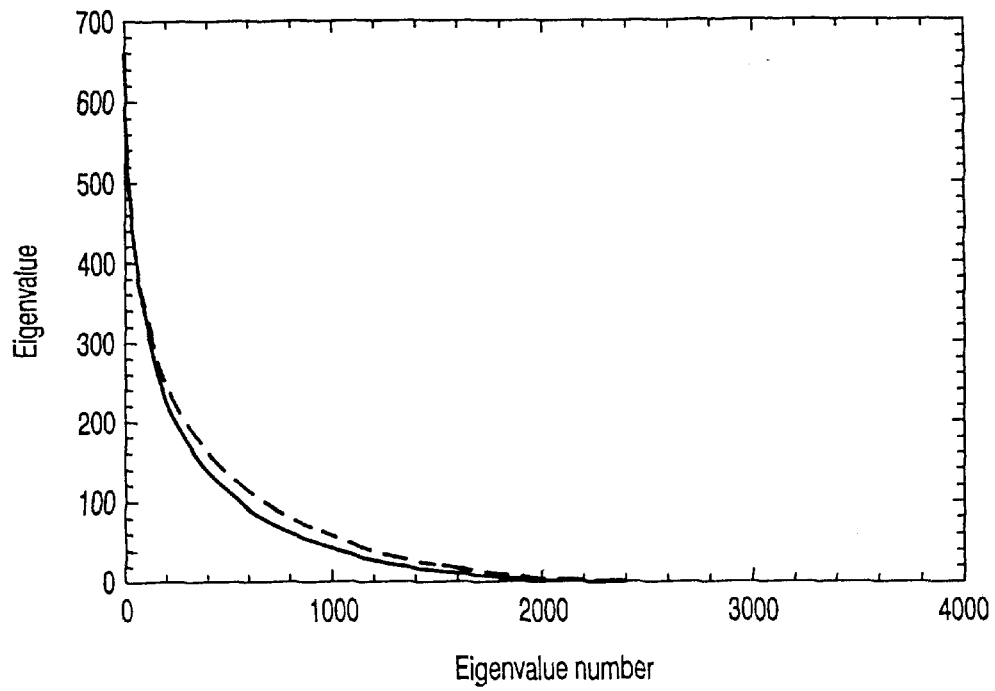
FIG. 3 is a graphic representation of the precision of the eigenvalues of the auxiliary matrix obtained by application of Fourier transformation.

FIG. 3 is a graphic representation of the accuracy of the eigenvalues of the auxiliary matrix obtained by application of Fourier transformation. As has already been explained with reference to FIG. 2, the eigenvalues of the partial auxiliary matrices can be found by determining the Fourier transform of an arbitrary row or the mean value of two or more rows, the eigenvalues then being equal to the Fourier coefficients thus found. Because the partial auxiliary matrices are not exactly Toeplitz matrices, an error is thus introduced; the magnitude of this error can be determined by comparing the approximated values with the exact eigenvalues. The order number of the eigenvalues is plotted horizontally in FIG. 3 and the associated eigenvalue is plotted vertically. The exact value is represented by the solid line and the approximated value by the dashed line. This Figure reveals suitable correspondence between the approximated and the exact eigenvalues.

Figure 4A:
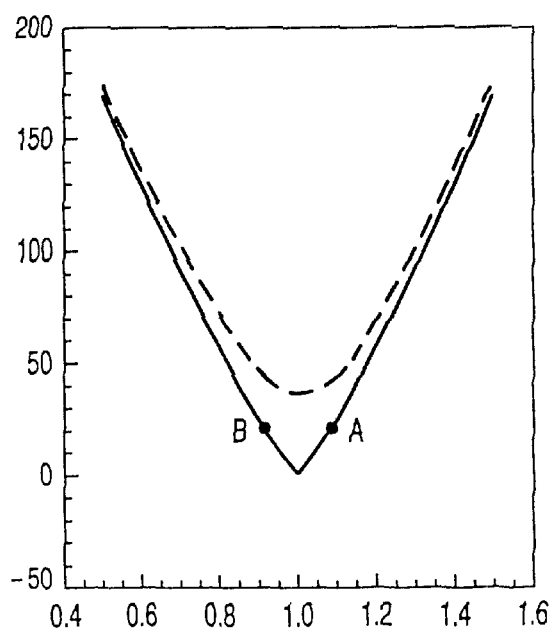
FIG. 4 is a graphic representation of the convergence problem occurring during minimizing of the functional F.

FIG. 4 is a graphic representation of the convergence problem during the minimizing of the functional F as described above. FIG. 4a shows, by way of the solid line, a situation with a comparatively steep course of the functional F around the minimum of F in dependence on one variable. During the determination of the minimum in dependence on said variable, for example, the process has reached the point A where it is determined that the convergence criterion has not yet been satisfied. A next iteration step may cause the process to reach the point B so that a jump beyond the minimum has been made and it is determined again that the convergence criterion has not yet been satisfied. During a subsequent iteration step the process may reach the original iteration point A again, or even a point situated further from the minimum. So it may occur that the minimum is not reached at all. The dashed line represents the effect of noise addition. It will be evident that a more regular course of the convergence curve is thus achieved, so that the described effect cannot occur.

Figure 4B:
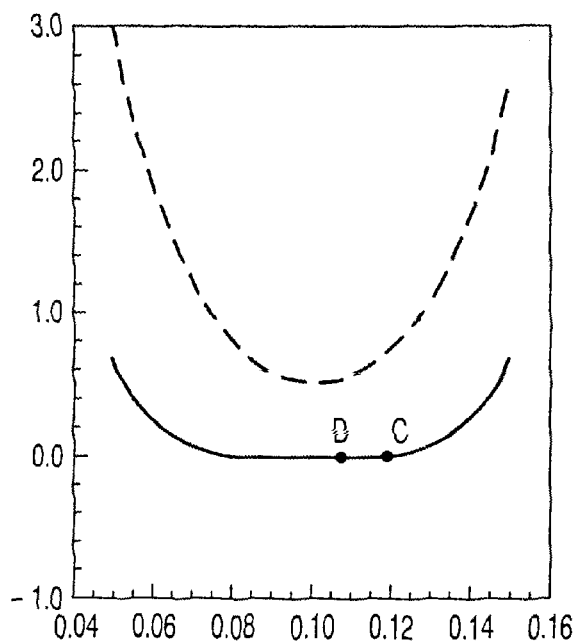

FIG. 4b shows the situation involving a comparatively flat course of the functional F around the minimum. During the determination of the minimum the process has then reached, for example the point C where it is determined that the convergence criterion has not yet been satisfied. A next iteration step may cause the process to reach the point D, so that the minimum has been further approached by a very small amount only. Therefore, it may occur that this forward progress is so small that it is incorrectly assumed that the convergence criterion has been satisfied, so that the minimizing process is terminated. So in this case it may also occur that the minimum is not reached at all. The dashed line represents the effect of noise addition. It will be evident that a less flat course of the convergence curve is thus achieved, so that the described effect cannot occur.

Figure 5:
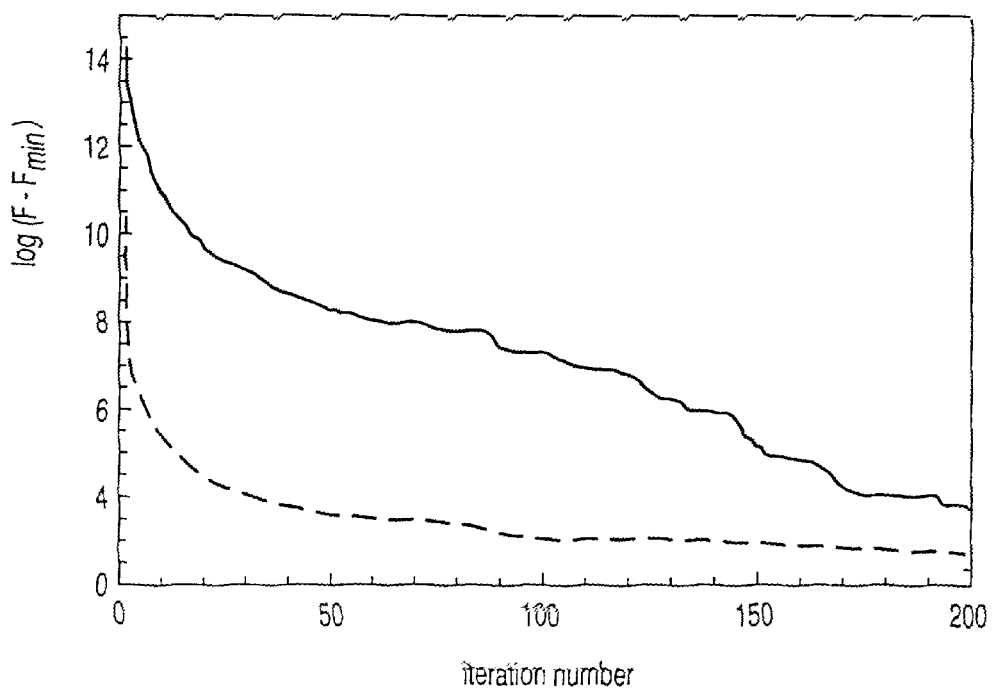
FIG. 5 is a graphic representation of the enhancement of the convergence during minimizing of the functional F by noise addition.

The effect of the noise addition is shown in FIG. 5. This Figure is a graphic representation of the enhancement of the convergence during the minimizing of the functional F by the noise addition. The solid line represents the situation without noise addition to the approximated intrinsic spectrum whereas the dashed line represents the situation with noise addition. The number of iterations is plotted horizontally and the logarithm of the difference between the actual value of the functional F and the minimum value is plotted vertically. The situation in the absence of noise is illustrated again: notably in the vicinity of the $80^{th}$ iteration, but further down a flat course can also be observed for the solid curve, indicating a slow convergence. This situation is significantly improved by noise addition as demonstrated by the dashed line: the final level of the minimizing process is reached already around the $100^{th}$ iteration for the dashed line, whereas for the solid line it is situated significantly beyond the $200^{th}$ iteration. The advantage will even be more evident if less severe accuracy requirements are imposed; when the process is terminated at a vertical value of 6, the situation with noise addition is already reached upon the fifth iteration, whereas without noise addition it is reached only upon the $150^{th}$ iteration.

What is claimed is:

1. A method of determining an intrinsic spectrum f of radiation emitted by an object to be examined, which intrinsic spectrum f is represented by a set of N data points $f_1 \ldots f_N$ and is determined from a measured spectrum h which is represented by a set of M measuring points $H_1 \ldots h_M$ and is measured by means of an analysis apparatus having a given apparatus transfer function G in the form of an M×N matrix, which method includes the following steps:

a) forming an approximated intrinsic spectrum g of N data points $g_1 \ldots g_N$;

b) determining a measure of misfit $\chi^2$ between the approximated intrinsic spectrum, convoluted with the apparatus transfer function G, and the measured spectrum;

c) determining the value of a predetermined regularizing function S by inserting the approximated intrinsic spectrum in this function;

d) forming a functional $F=\chi^2+\alpha S$ containing a regularizing constant $\alpha$;

e) solving the regularizing constant $\alpha$ from said functional, the N eigenvalues $\lambda_1 \ldots \lambda_N$ of an N×N auxiliary matrix A formed from the apparatus transfer function and the approximated intrinsic spectrum being determined during said solution process;

f) executing a minimizing process on the functional F with the last regularizing constant $\alpha$ found, using the N data points of the intrinsic spectrum as variables, the N data points thus found constituting a next approximated intrinsic spectrum;

g) repeating the steps b) to f), if necessary, until a predetermined convergence criterion has been satisfied;

h) identifying the approximated intrinsic spectrum then valid as the intrinsic spectrum searched; characterized in that for the determination of the N eigenvalues $\lambda_1 \ldots \lambda_N$ N of the N×N auxiliary matrix A, the auxiliary matrix is subdivided into a number of L partial auxiliary matrices $P_j$ (j=1 . . . L) which are situated around the diagonal of the auxiliary matrix A, and that the eigenvalues of each partial auxiliary matrix $P_j$ are determined separately, the set of eigenvalues $\lambda_1 \ldots \lambda_N$ of the N×N auxiliary matrix A consisting of the set of all eigenvalues of the partial auxiliary matrices $P_j$.

2. A method as claimed in claim 1, wherein the eigenvalues of the partial auxiliary matrices $P_j$ are determined by determining the Fourier transform of an arbitrary row of each of said partial auxiliary matrices.

3. A method as claimed in claim 1, wherein the eigenvalues of the partial auxiliary matrices $P_j$ are determined by determining the Fourier transform of the mean of at least two arbitrary rows of each of said partial auxiliary matrices.

4. A method as claimed in claim 1, wherein an amount which is arbitrarily distributed among the measuring points is added to the measuring points of the set of N measuring points $h_1 \ldots h_M$ during the execution of the minimizing process.

* * * * *